United States Patent [19]

Miyake et al.

[11] Patent Number: 5,208,399
[45] Date of Patent: May 4, 1993

[54] METHOD FOR PRODUCING ALLYL CHLORIDE

[75] Inventors: Takanori Miyake, Yokkaichi; Kazunari Hirakawa, Kurume; Makoto Hanaya, Yokkaichi; Junichi Kawamura, Yamaguchi, all of Japan

[73] Assignee: Tosoh Corporation, Shinnanyo, Japan

[21] Appl. No.: 757,193

[22] Filed: Sep. 10, 1991

[30] Foreign Application Priority Data

| Sep. 10, 1990 | [JP] | Japan | 2-237011 |
| Sep. 10, 1990 | [JP] | Japan | 2-237012 |
| Sep. 11, 1990 | [JP] | Japan | 2-239071 |
| Sep. 11, 1990 | [JP] | Japan | 2-239072 |
| Sep. 12, 1990 | [JP] | Japan | 2-240081 |
| Sep. 12, 1990 | [JP] | Japan | 2-240082 |
| Jul. 29, 1991 | [JP] | Japan | 3-210473 |

[51] Int. Cl.$^5$ .................... C07C 11/15; C07C 17/156
[52] U.S. Cl. .................................................. 570/224
[58] Field of Search ........................................ 570/224

[56] References Cited

U.S. PATENT DOCUMENTS 3,462,502  8/1969  Hornig et al. ................ 570/224

FOREIGN PATENT DOCUMENTS 1155281  6/1969  United Kingdom .
1174509  12/1969  United Kingdom .
1251535  10/1971  United Kingdom ................ 570/224

OTHER PUBLICATIONS

Flid et al C.A. vol. 76:45701q 1972.
Shell C.A. vol. 77:151436n 1972.

*Primary Examiner*—Howard T. Mars
*Attorney, Agent, or Firm*—Oblon, Spivak, McClelland, Maier & Neustadt

[57] ABSTRACT

A method for producing allyl chloride by oxychlorination of propylene, which comprises reacting propylene, hydrogen chloride and oxygen in the presence of a catalyst comprising an alloy of tellurium supported on a carrier.

10 Claims, 5 Drawing Sheets

METHOD FOR PRODUCING ALLYL CHLORIDE

The present invention relates to a method for producing allyl chloride which is useful in the industry of organic chemistry.

Allyl chloride is a very important compound as a starting material for an epichlorohydrin or as an intermediate for the production of various organic compounds.

At present, allyl chloride is produced by a noncatalytic thermal chlorination reaction at a high temperature of a level of from 450° to 500° C. using propylene and chlorine as starting materials. In the non-catalytic thermal chlorination reaction, a large quantity of energy is required because of the reaction at such a high temperature, hydrogen chloride is produced as a by-product, and due to deposition of carbonaceous residue, the reactor is required to be regenerated periodically. Thus, the thermal chlorination reaction has many points which require improvements.

Under the circumstances, a study is being made in an attempt to produce allyl chloride catalytically at a relatively low temperature of a level of from 200° to 300° C. by means of a catalyst. For example, Japanese Examined Patent Publication No. 34569/1973 discloses a method for preparing allyl chloride by oxychlorination of propylene at 200° C. by means of a catalyst supported on an active carbon, prepared by using a solution having tellurium oxide and cupric chloride dissolved in hydrochloric acid, and it is stated therein that nickel, lead, silver and a platinum-group metal may be used instead of copper.

Further, Dutch Patent 7108153 discloses a method wherein an oxychlorination reaction of propylene is conducted at 240° C. by means of a three-component catalyst comprising tellurium tetrachloride, cupric chloride and potassium chloride supported on silica gel; German Patent 1300930 discloses a method wherein an oxychlorination reaction of propylene is conducted at 350° C. by means of a three-component catalyst comprising palladium chloride, cupric chloride and potassium chloride supported on γ-alumina; and Japanese Unexamined Patent Publication No. 1504/1964 discloses a method wherein an oxychlorination reaction of propylene is conducted at 200° C. by using, as a catalyst, active carbon having rhodium, palladium, platinum or iridium supported thereon.

As disclosed in the above references, it is well known to produce allyl chloride by an oxychlorination reaction of propylene by means of a catalyst having a tellurium compound, a copper salt or a platinum-group metal supported on active carbon, silica or alumina.

Under these circumstances, the present inventors have conducted a detailed study on oxychlorination of propylene and, as a result, have unexpectedly found a new fact that when a catalyst comprising an alloy of tellurium, or an alloy of tellurium and an alkali metal salt, supported on a carrier, is used, allyl chloride can be obtained at high levels of catalytic activity and selectivity. The present invention has been accomplished on the basis of this discovery.

Thus, the present invention provides a method for producing ally chloride by oxychlorination of propylene, which comprises reacting propylene, hydrogen chloride and oxygen in the presence of a catalyst comprising an alloy of tellurium, or an alloy of tellurium and an alkali metal salt, supported on a carrier.

Now, the present invention will be described in detail with reference to the preferred embodiments.

In the method of the present invention, a catalyst comprising an alloy of tellurium, or an alloy of tellurium and an alkali metal salt, supported on a carrier, is used.

The amount of tellurium supported and constituting the alloy of tellurium can not generally be defined, since it varies depending upon the reaction conditions such as the reaction temperature and the flow rate of the feed material gas, but it is usually within a range of from 0.1 to 50% by weight, more preferably from 0.1 to 20% by weight, to the total amount by weight of the catalyst (inclusive of the carrier). If the supported amount exceeds 50% by weight, no substantial increase in the effects can be expected. On the other hand, if the supported amount is less than 0.1%, no adequate catalytic activity can be obtained.

There is no particular restriction as to the other component constituting the alloy (hereinafter referred to simply as "the other component") so long as it is capable of forming an alloy with tellurium. For example, it may be a member selected from the group consisting of metals of Groups VIII, Va and Ib of the Periodic Table. Specific examples include, for example, Group VIII metals such as iron, cobalt, nickel, palladium, ruthenium and iridium, Group Va metals such as antimony and bismuth, and Group Ib metals such as copper.

The supported amount of the other component alloyed to tellurium may be defined by an atomic ratio to tellurium. Namely, the atomic ratio of tellurium to the other component is usually within a range of from 40:1 to 1:20, preferably from 20:1 to 1:15.

If the atomic ratio of tellurium to the other component exceeds 40, no adequate effects by alloying are likely to be obtained. On the other hand, if the atomic ratio of the other component to tellurium exceeds 20, a problem is likely to occur with respect to the catalytic activity and selectivity.

In the method of the present invention, a catalyst having a tellurium alloy supported on a carrier or having a tellurium alloy and an alkali metal salt supported on a carrier, is used. When the alkali metal salt is also present, there is no particular restriction as to the alkali metal salt to be used so long as the tellurium alloy and the alkali metal salt are coexistent on the carrier, and various alkali metal salts may be employed. The alkali metal salt may be an alkali metal inorganic salt such as an alkali metal chloride, nitrate, sulfate, acetate or oxide. More specifically, it may be a chloride such as lithium chloride, sodium chloride, potassium chloride or cesium chloride, a nitrate such as potassium nitrate or a cesium nitrate, a sulfate such as potassium sulfate or a cesium sulfate, or an acetate such as potassium acetate or cesium acetate. Various organic salts may also be used. For example, organic salts such as naphthenates and oxalates may be mentioned as typical examples. Among them, there may be some which will be converted to other compounds during the reaction, depending upon the types of the salts.

The alkali metal salt is used usually in an amount of from 0.01 to 30% by weight, preferably from 0.05 to 20% by weight, to the total amount by weight of the carrier, the tellurium alloy and the alkali metal salt. If the amount is less than 0.01% by weight, no adequate effects tend to be obtained. On the other hand, if it exceeds 30% by weight, the catalytic activity per unit weight tends to be low.

When the alkali metal salt is used, there is no particular restriction as to the method for supporting it on the carrier. For example, the tellurium alloy may be formed first on the carrier and then the alkali metal salt may be supported. Inversely, the alkali metal salt may be supported first, and then the tellurium alloy may be formed on the carrier. Further, starting materials of tellurium and the other component may be supported at the same time as the alkali metal salt, and then the alloy of tellurium may be formed.

The tellurium material to be used in the method of the present invention may be tellurium metal itself, and there is no particular restriction so long as it can be converted to metallic tellurium by the operation for alloying. As the material to be converted to metallic tellurium by the alloying operation, an inorganic tellurium compound such as telluric acid, tellurium chloride, tellurium oxychloride or tellurium dioxide, or an organic tellurium compound such as a monoalkyl telluride, a dialkyl telluride or an alkyl tellurium chloride, may be mentioned. Likewise, the material for the other component constituting an alloy with tellurium, may be the metal of the other component itself, or may be a material which can be converted to the metal by the alloying operation. As a specific example of such a compound, an inorganic compound such as a chloride, nitrate, sulfate, acetate or oxide, or an organic compound such as a naphthenate, stearate or oxalate, of the other component, may be mentioned.

In the method of the present invention, the catalyst component is used as supported on a carrier. The carrier is not particularly limited so long as it does not adversely affect the performance of the catalyst composed of the tellurium alloy, or the tellurium alloy and the alkali metal salt. For example, from the viewpoint of whether the catalyst is acidic or basic, it may be a silica carrier which is regarded as neutral, or it may be an alumina carrier which is usually regarded as acidic. Otherwise, a magnesia carrier which is usually regarded as basic may be used as the carrier. Further, zirconia, titania or active carbon may be mentioned as other examples.

In the method of the present invention, a catalyst having an alloy formed by tellurium and the other component on the carrier, or a catalyst having the tellurium alloy and the alkali metal salt supported on the carrier, is employed. There is no particular restriction as to the method of alloying to form the alloy of tellurium, so long as the alloy supported on a carrier is finally obtainable.

As the alloying method, a method wherein metallic tellurium and the other component in a metallic form are physically mixed with the carrier, followed by forming the alloy by e.g. heating, a method wherein either a tellurium compound or a compound of the other component is supported firstly on the carrier, and the rest is then supported, followed by alloying, or a method wherein both the tellurium compound and the compound of the other component are simultaneously supported, followed by alloying, may, for example, be mentioned. As mentioned above, when the alkali metal salt is used in combination with the tellurium alloy, such an alkali metal salt may be preliminarily supported on the carrier, or it may be supported after supporting the respective components of the alloy. Otherwise, it may be supported after formation of the alloy.

In a case other than the case where metallic tellurium and a metal of the other component are used as starting materials, the tellurium compound and/or the compound of the other component has to be supported on the carrier. However, there is no particular restriction as to the method for supporting it. For example, the tellurium compound and/or the compound of the other component may be physically mixed with the carrier for supporting. Otherwise, the tellurium compound and/or the compound of the other component may be supported by a so-called impregnation method wherein the tellurium compound and/or the compound of the other component may be dissolved preliminarily in a suitable solvent, and the carrier is impregnated in this solution. There is no particular restriction as to the solvent to be used for such impregnation method, so long as it is capable of dissolving the tellurium compound and/or the compound of the other component. However, water, an acid such as hydrochloric acid or nitric acid, or an organic solvent such as acetone or ethanol, may, for example, be used.

In a case other than the case where metallic tellurium and a metal of the other component are used as the starting materials, it is necessary to reduce the tellurium compound and/or the compound of the other component supported on the carrier. There is no particular restriction as to the reducing agent, so long as it is capable of reducing the tellurium compound and/or the compound of the other component to a zero valence. As a typical example of such a reducing agent, an inorganic gaseous reducing agent such as hydrogen or carbon monoxide, an olefin such as propylene, an alcohol such as methanol, a formic acid compound such as formic acid or a formic ester, or hydrazine or lithium aluminum hydride, may be mentioned.

For the alloying by means of such a reducing agent, it is necessary to conduct alloying at a temperature whereby the tellurium compound and/or the compound of the other component can be reduced to a zero valence. The alloying temperature can not generally be defined, since it varies depending upon the reducibility of the materials for the tellurium and/or the other component. However, it is usually from 0° C. to 1,000° C., preferably from 20° C. to 800° C. If the temperature is lower than 0° C., it becomes difficult to reduce the tellurium compound and/or the compound of the other component to a zero valence, and in some cases, alloying can not be accomplished. On the other hand, if it exceeds 1,000° C., the alloy formed tends to undergo crystal growth, whereby the activities of the finally obtained catalyst tend to be low.

There is no particular restriction as to the alloying method, and it can be conducted in a gas phase or a liquid phase. In the case of gas phase alloying, a gas composed of a reducing agent or a gas containing a reducing agent may be passed through the precursor of the catalyst to be alloyed. On the other hand, in the case of liquid phase alloying, the precursor of the catalyst is contacted with a liquid of a reducing agent or a liquid containing a reducing agent in a batch system or in a liquid circulating system for alloying. It is, of course, possible to conduct the reduction and the alloying under separate conditions. For example, the tellurium and the other component may be reduced to a zero valence at a relatively low temperature, and then alloying may be conducted in an inert gas atmosphere at a high temperature.

In the method of the present invention, a catalyst having a tellurium alloy supported on the carrier is employed irrespective of the presence or absence of the alkali metal salt. Formation of the alloy can be ascertained, for example, by a usual X-ray diffraction analysis or by a scanning transmission electron microscope (STEM). In the X-ray diffraction, the formation can be examined on the basis of whether a diffraction pattern characteristic to the alloy is obtainable. In this case, the ratio in the relative intensity of the obtained peaks may vary depending upon the alloying method.

In the method of the present invention, the reaction for the production of allyl chloride by oxychlorination of propylene may be conducted in a liquid phase or a gas phase. However, a gas phase is preferred.

The reaction temperature for the gas phase reaction can not generally be defined, since it varies depending upon the performance of the catalyst. However, it is typically from 100° to 400° C., preferably from 100° to 350° C. If the reaction temperature is lower than 100° C., no adequate activities tend to be obtained. On the other hand, if it exceeds 400° C., formation of by-products tends to be substantial, whereby the selectivity for desired allyl chloride tends to be low.

Likewise, the reaction pressure can not generally be defined, since the necessary pressure varies depending upon the performance of the catalyst. However, it is typically within a range of from atmospheric pressure to 50 atm, preferably from atmospheric pressure to 30 atm. If the reaction pressure exceeds 50 atom, no substantial increase in the effect will be obtained by the increase of the pressure, and such tends to be economically disadvantageous.

In the method of the present invention, propylene, hydrogen chloride and oxygen are used as feed materials for the reaction. A diluting gas may be employed, as the case requires. As such a diluting gas, any gas inert to the reaction may be employed. For example, nitrogen or argon may be employed. The respective feed materials may be used without any particular restriction, so long as they are industrially available. The respective feed materials may be used typically in the proportions of the following ranges represented by volume %.
Propylene: 4-90%
Hydrogen chloride: 1-50%
Oxygen: 1-50%
Diluting gas: 0-90% If the proportions of propylene, hydrogen chloride and oxygen are less than the respective lower limits, no adequate reaction rate for industrial operation will be obtained. Further, if hydrogen chloride exceeds the upper limit, formation of byproducts tends to be substantial. If oxygen exceeds the upper limit, the combustion product tends to be substantial.

The supply rate of the feed material gas can not generally be defined, since its range varies depending upon the performance of the catalyst or upon the selectivity or the formation rate of the product. However, the reaction can be conducted within a range of from 100 to 50,000 h$^{-1}$ as represented by the flow rate of the feed material gas to the volume of the catalyst layer i.e. by the gas space velocity (SV). If SV is less than 100, it tends to be hardly possible to obtain an industrially satisfactory production rate of allyl chloride. On the other hand, if SV exceeds 50,000, the conversion of the feed material tends to be low, and such will be economically disadvantageous.

In the method of the present invention, the reaction can be conducted by any one of a fixed bed system, a fluidized bed system or a mobile bed system.

Now, the present invention will be described in further detail with reference to Examples. However, it should be understood that the present invention is by no means restricted by such specific Examples.

EXAMPLE 1

To 250 ml of 1N nitric acid, 25 g of active carbon having 5% of water adsorped thereon (Ryujo Shirasagi C, manufactured by Takeda Chemical Industries, Ltd) was added and treated at 80° C. for 3 hours under reflux. The aqueous solution was filtered, and the remaining active carbon was washed with warm water of 98° C. until the pH became 6. The obtained active carbon was dried at 80° C. for one day, then heated from room temperature to 300° C. at a rate of 10° C. per minute under a nitrogen stream of 300 ml/min and subjected to heat treatment at 300° C. for 3 hours. Then, 1.23 g of cobalt dichloride hexahydrate and 1.39 g of tellurium tetrachloride were dissolved in 40 ml of a 6N hydrochloric acid aqueous solution, and to this aqueous solution, 10 g of the active carbon treated as above was added. Upon expiration of 20 hours, the hydrochloric acid solution was dried over a warm bath of 60° C. Further, drying was conducted in a glass tube where the temperature was raised from room temperature to 150° C. at a rate of 10° C. per minute under a nitrogen stream and then maintained at 150° C. for one hour. Then, in that state, the temperature was lowered to room temperature. The nitrogen stream was replaced by a gas comprising 10% of hydrogen and the rest being nitrogen, and the total flow rate was adjusted to be 200 ml/min. The temperature was raised from room temperature to 150° C. at a rate of 10° C. per minute and then maintained at 150° C. for two hours. Further, the temperature was raised to 400° C. at a rate of 10° C. per minute and then maintained at 400° C. for one hour to obtain a Te-Co alloy catalyst supported on active carbon. The amount of supported Te of the catalyst thus prepared was 6% as metal, and the atomic ratio of tellurium to cobalt was 1. The catalyst thus obtained was analyzed by X-ray diffraction, whereby it was confirmed that a catalyst having the X-ray diffraction pattern of CoTe as shown in Table 1 was formed. A 2 g portion of the catalyst thus obtained was packed in a fixed bed flow type reactor made of glass, and a gas mixture of propylene:hydrogen chloride:oxygen:nitrogen=2:2:1:2 was supplied at a SV of 670 per hour. The temperature was raised to a predetermined temperature and held at that temperature for 30 minutes, and the product was analyzed by gas chromatography. The results are shown in Table 2.

EXAMPLES 2 TO 6

As in Example 1, Te-Ni Te-Cu, Te-Ir, Te-Pt and Te-Rh alloy catalysts supported on active carbon were, respectively, prepared in the same manner except that nickel nitrate hexahydrate, cupric chloride dihydrate, iridium chloride monohydrate, chloroplatinic acid hexahydrate and rhodium chloride trihydrate were used, respectively, instead of the cobalt salt, and the amount of tellurium tetrachloride was adjusted. The amount of supported tellurium in the obtained catalysts was 6%, and the atomic ratio of tellurium to the respective metals was 1. Using each catalyst thus obtained, the reaction was conducted in the same manner as in Example 1. The results are shown in Table 2.

EXAMPLE 7

Figure 1:
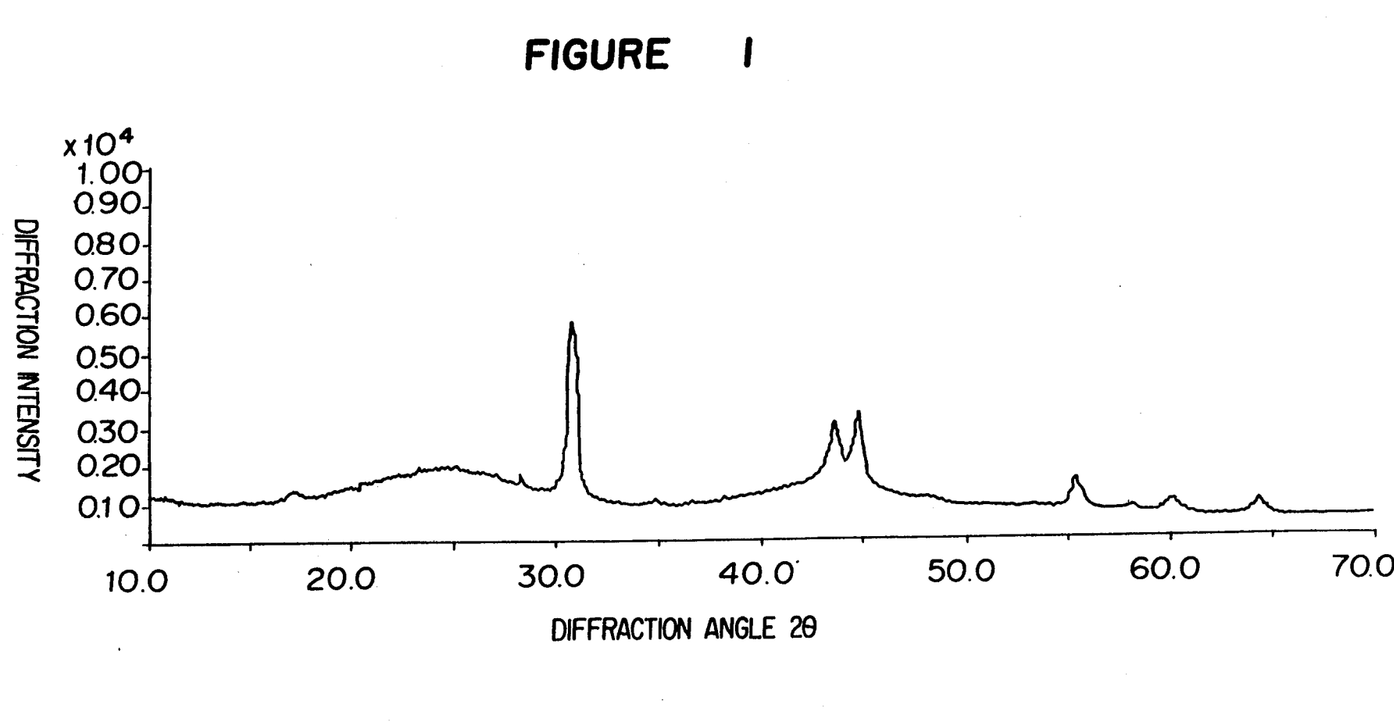
FIG. 1 is an X-ray diffraction pattern of a $PdTe_2$ alloy catalyst supported on active carbon analyzed by an X-ray diffraction apparatus (40 KV, 24 mA, copper Kα-line), wherein the abscissa represents the diffraction angle $2\theta$ and the ordinate represents the diffraction intensity.

A Te-Pt alloy catalyst supported on active carbon was prepared in the same manner as in Example 1 except that 0.456 g of palladium chloride and 1.39 g of tellurium tetrachloride were used. The amount of supported Te in the catalyst thus prepared was 6% as metal, and the atomic ratio of tellurium to palladium was 2. The catalyst thus obtained was analyzed by X-ray diffraction, whereby it was confirmed that a catalyst having the X-ray diffraction pattern of $PdTe_2$ as shown in Table 3 and in FIG. 1, was formed. Using 2 g of the catalyst thus obtained, the reaction was conducted in the same manner as in Example 1. The results are shown in Table 4.

EXAMPLE 8

A Te-Pd alloy catalyst supported on active carbon was prepared in the same manner as in Example 1 except that 0.937 g of palladium chloride and 1.42 g of tellurium tetrachloride were used. The amount of supported Te in the catalyst thus prepared, was 6% as metal, and the atomic ratio of tellurium to palladium was 1. Using 2 g of this catalyst, the reaction was conducted in the same manner as in Example 1. The results are shown in Table 4.

EXAMPLE 9

A Te-Pd alloy catalyst supported on active carbon was prepared in the same manner as in Example 1 except that 1.057 g of palladium chloride and 0.65 g of tellurium tetrachloride were used. The amount of supported Te in the catalyst thus prepared, was 2.8% as metal, and the atomic ratio of tellurium to palladium was 0.48. Using 2 g of this catalyst, the reaction was conducted in the same manner as in Example 1. The results are shown in Table 4.

EXAMPLE 10

A Te-Pd alloy catalyst supported on active carbon was prepared in the same manner as in Example 1 except that the amount of supported tellurium became 1% while the atomic ratio of tellurium to palladium was maintained to be 1, and using 2 g of the catalyst thus obtained, the reaction was conducted in the same manner as in Example 1. The results are shown in Table 4.

EXAMPLE 11

A Te-Pd alloy catalyst supported on active carbon was prepared in the same manner as in Example 1 except that active carbon prepared by conducting no nitric acid treatment, basing the temperature from room temperature to 300° C. at a rate of 10° C. per minute under a nitrogen stream of 300 ml/min and conducting heat treatment at 300° C. for 3 hours, was used as the carrier and the amount of palladium chloride was changed to 0.937 g and the amount of tellurium tetrachloride was changed to 1.42 g, and using 2 g of the obtained catalyst, the reaction was conducted in the same manner as in Example 1. The results are shown in Table 4.

EXAMPLES 12 TO 16

Various Te-Pd alloy catalysts were prepared in the same manner as in Example 8 except that α-alumina, γ-alumina, titania, magnesia and silica were used, respectively, instead of active carbon, and using 2 g of the catalyst thus obtained, the reaction was conducted in the same manner as in Example 1. Results are shown in Table 4.

EXAMPLE 17

A catalyst was prepared in the same manner as in Example 1 except that a solution having 1.186 g of palladium acetate and 1.42 g of tellurium tetrachloride dissolved in 80 ml of acetone, was used. The amount of supported Te in the catalyst thus prepared was 6% as metal, and the atomic ratio of tellurium to palladium was 1. The reaction was conducted in the same manner as in Example 1 except that 2 g of this catalyst was used. The results are shown in Table 4.

EXAMPLE 18

A Te-Ru alloy catalyst supported on active carbon was prepared in the same manner as in Example 1 except that 0.671 g of ruthenium chloride trihydrate and 1.38 g tellurium tetrachloride were used. The amount of supported Te in the catalyst thus prepared was 6% as metal, and the atomic ratio of tellurium to ruthenium was 2. The catalyst thus obtained was analyzed by X-ray diffraction, whereby it was confirmed that a catalyst having the X-ray diffraction pattern of $RuTe_2$ as shown in Table 5, was formed. Using 2 g of the catalyst thus obtained, the reaction was conducted in the same manner as in Example 1. The results are shown in Table 6.

EXAMPLE 19

Figure 2:
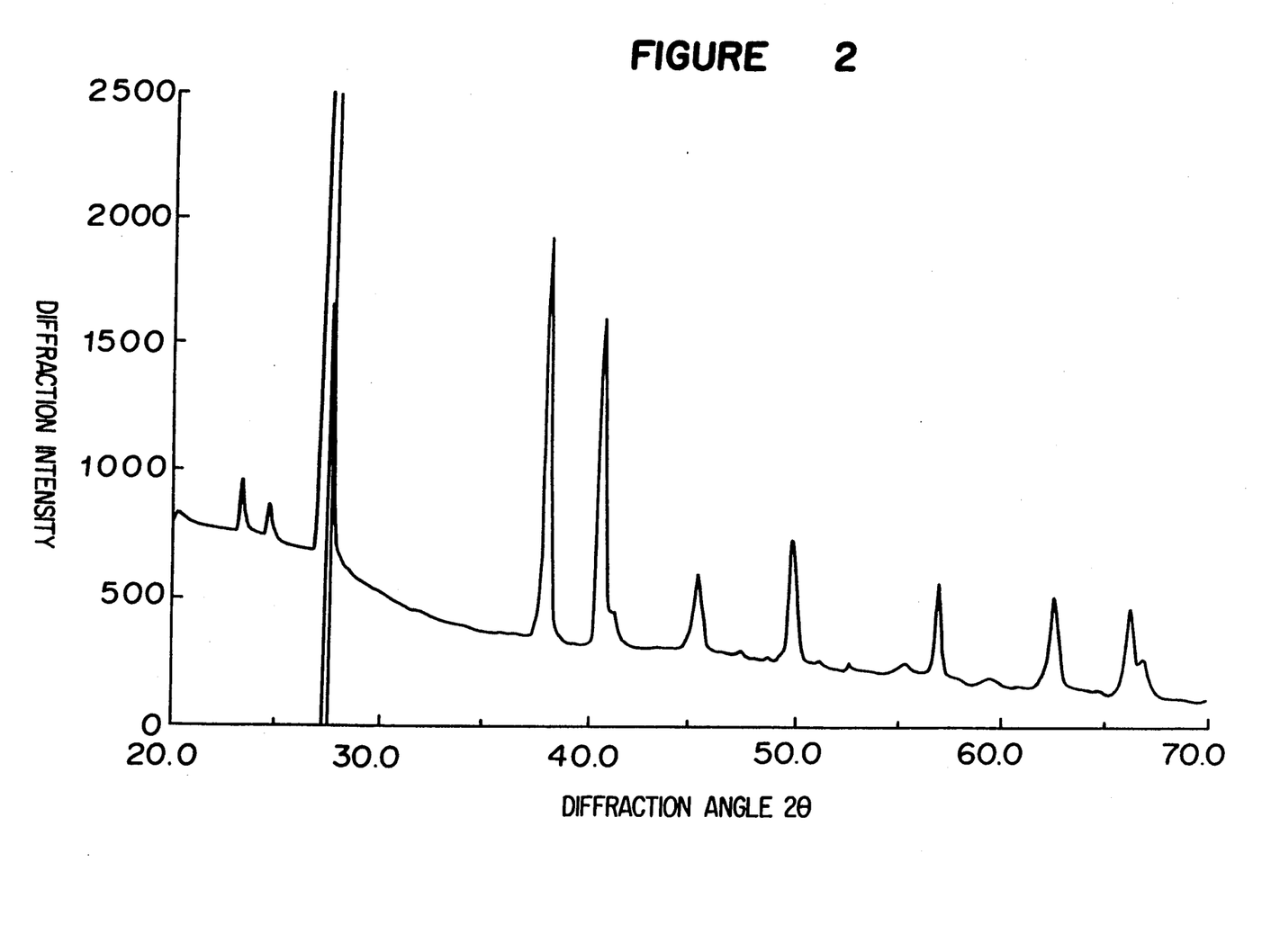
FIG. 2 is a similar X-ray diffraction pattern of a BiTe alloy catalyst supported on active carbon.

A Te-Bi alloy catalyst supported on active carbon was prepared in the same manner as in Example 1 except that 1.762 g of bismuth tetrachloride and 1.51 g tellurium tetrachloride were used, and the temperature for the reduction by hydrogen and alloying was changed to 250° C. The amount of supported Te in the catalyst thus prepared was 6% as metal, and the atomic ratio of tellurium to bismuth was 1. The catalyst thus obtained was analyzed by X-ray diffraction, whereby it was confirmed that a catalyst having the X-ray diffraction pattern of BiTe as shown in Table 7 and in FIG. 2, was formed. Using 2 g of the catalyst thus obtained, the reaction was conducted in the same manner as in Example 1. The results are shown in Table 8.

EXAMPLE 20

Figure 3:
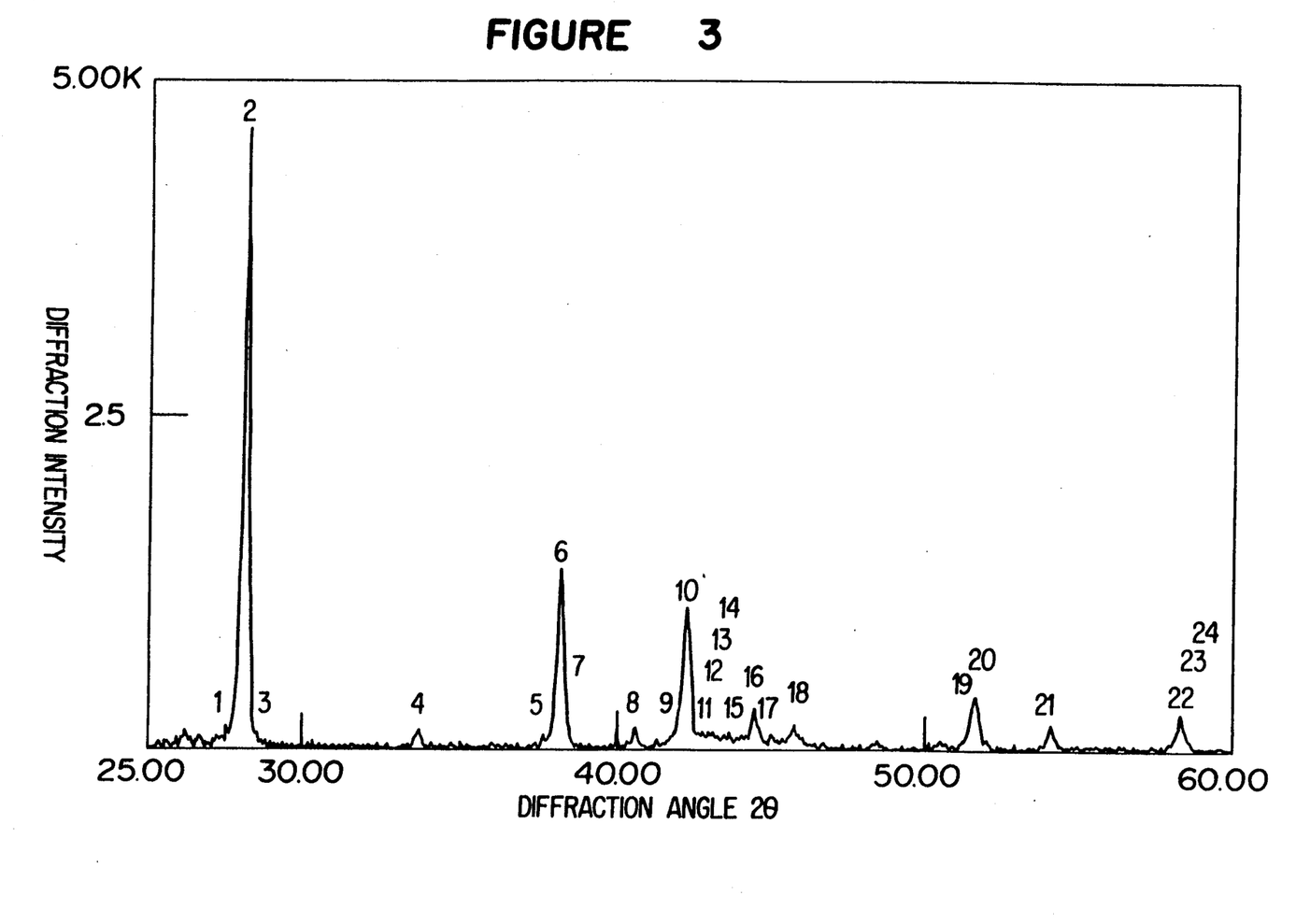
FIG. 3 is a similar X-ray diffraction pattern of a $Sb_2Te_3$ alloy catalyst supported on active carbon.

A Te-Sb alloy catalyst supported on active carbon was prepared in the same manner as in Example 1 except that 0.793 g of antimony trichloride and 1.41 g of tellurium tetrachloride were used, and the temperature for the reduction by hydrogen and alloying was changed to 550° C. The amount of supported Te in the catalyst thus prepared was 6%, and the atomic ratio of tellurium to antimony was 1.5. The catalyst thus obtained was analyzed by X-ray diffraction, whereby it was confirmed that a catalyst having the X-ray diffraction pattern of $Sb_2Te_3$ as shown in Table 9 and in FIG. 3, was formed. Using 2 g of the catalyst thus obtained, the reaction was conducted in the same manner as in Example 1. The results are shown in Table 10.

EXAMPLE 21

A Te-Sb alloy catalyst supported on active carbon was prepared in the same manner as in Example 1 except that 2.599 g of antimony trichloride and 1.54 g of tellurium tetrachloride were used, and the temperature for the reduction by hydrogen and alloying was changed to 400° C. The amount of supported Te in the catalyst thus prepared was 6% as metal, and the atomic ratio of tellurium to antimony was 0.5. Using 2 g of the catalyst, the reaction was conducted in the same manner as in Example 1 except that the composition of the gas mixture was changed to propylene:hydrogen chloride:oxygen:nitrogen=10:1:2:1 without changing the gas flow rate. The results are shown in Table 10.

EXAMPLE 22

Figure 4:
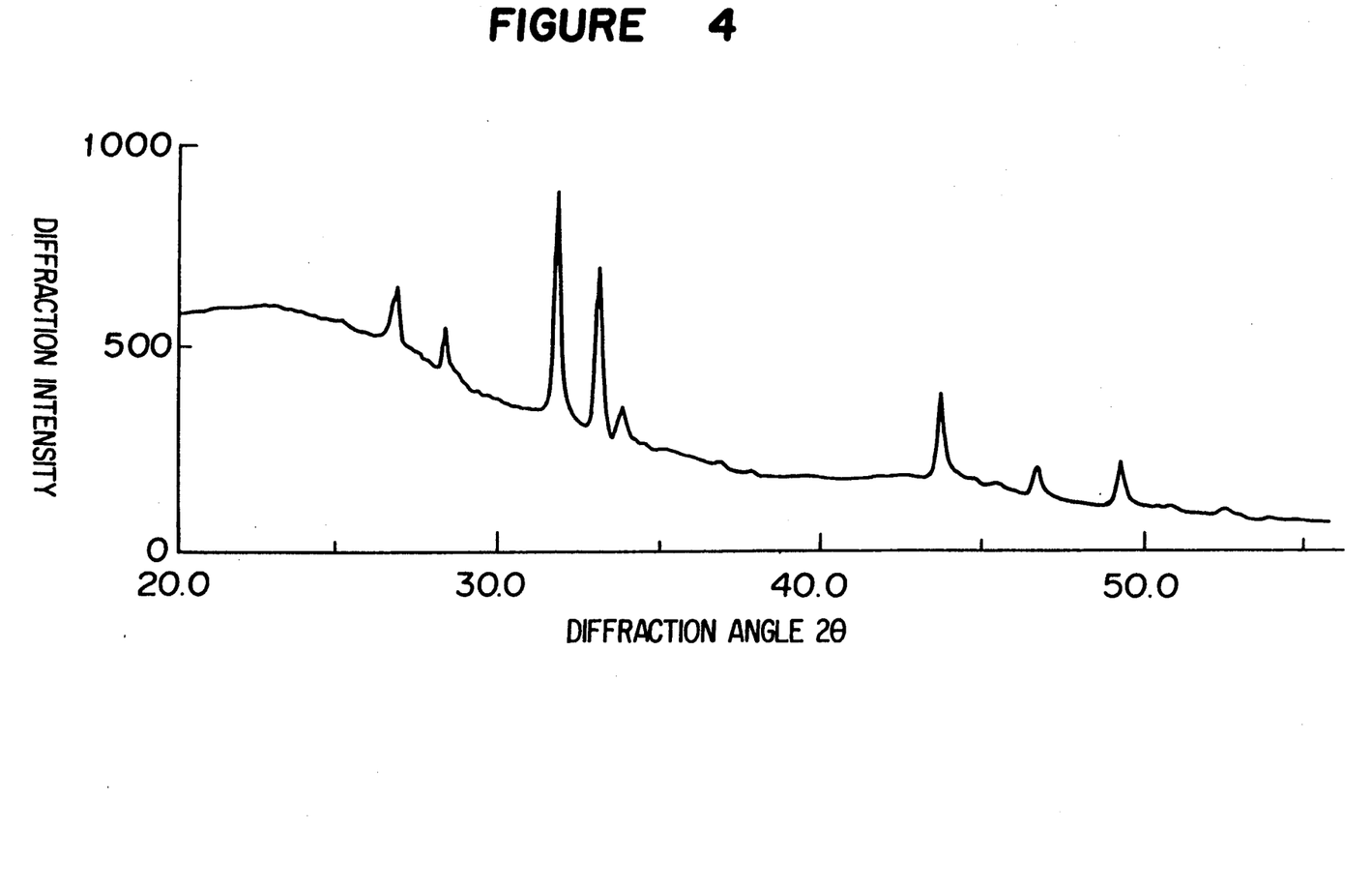
FIG. 4 is a similar X-ray diffraction pattern of a $FeTe_2$ alloy catalyst supported on active carbon.

A Te-Fe alloy catalyst supported on active carbon was prepared in the same manner as in Example 1 except that 0.411 g of ferric chloride anhydride and 1.367 g of tellurium tetrachloride were used. The amount of supported Te in the catalyst thus prepared was 6% as metal, and the atomic ratio of tellurium to iron was 2. The catalyst thus obtained was analyzed by X-ray diffraction, whereby it was confirmed that a catalyst having the X-ray diffraction pattern of $FeTe_2$ as shown in Table 11 and in FIG. 4, was formed. Using 2 g of the catalyst thus obtained, the reaction was conducted in the same manner as in Example 1. The results are shown in Table 12.

EXAMPLE 23

A Te-Fe alloy catalyst supported on active carbon was prepared in the same manner as in Example 1 except that 0.835 g of ferric chloride anhydride and 1.387 g of tellurium tetrachloride were used. The amount of supported Te in the catalyst thus prepared was 6% as metal, and the atomic ratio of tellurium to iron was 1. Using 2 g of the catalyst, the reaction was conducted in the same manner as in Example 1 except that SV was changed to 2,400 per hour by changing the amount of the catalyst without changing the total amount of supplied gas. The results are shown in Table 12.

EXAMPLE 24

A Te-Fe alloy catalyst supported on active carbon was prepared in the same manner as in Example 1 except that 0.204 g of ferric chloride anhydride and 1.358 g of tellurium tetrachloride were used. The amount of supported Te in the catalyst thus prepared was 6%, and the atomic ratio of tellurium to iron was 4. Using 2 g of this catalyst, the reaction was conducted in the same manner as in Example 1. The results are shown in Table 12.

EXAMPLE 25

A Te-Fe alloy catalyst supported on active carbon was prepared in the same manner as in Example 1 except that 0.0815 g of ferric chloride anhydride and 1.352 g of tellurium tetrachloride were used. The amount of supported Te in the catalyst thus prepared was 6%, and the atomic ratio of tellurium to iron was 10. Using 2 g of this catalyst, the reaction was conducted in the same manner as in Example 1. The results are shown in Table 12.

EXAMPLE 26

Using 2 g of the catalyst prepared in Example 22, the reaction was conducted in the same manner as in Example 1 except that the composition of the gas mixture was adjusted to propylene:hydrogen chloride:oxygen:nitrogen =4:2:1:0 without changing the total amount of supplied gas. The results are shown in Table 12.

EXAMPLE 27

Using 2 g of the catalyst prepared in Example 22, the reaction was conducted in the same manner as in Example 1 except that the composition of the gas mixture was changed to propylene:hydrogen chloride:oxygen:nitrogen=10:2:1:1 without changing the total amount of supplied gas. The results are shown in Table 12.

Example 28

Figure 5:
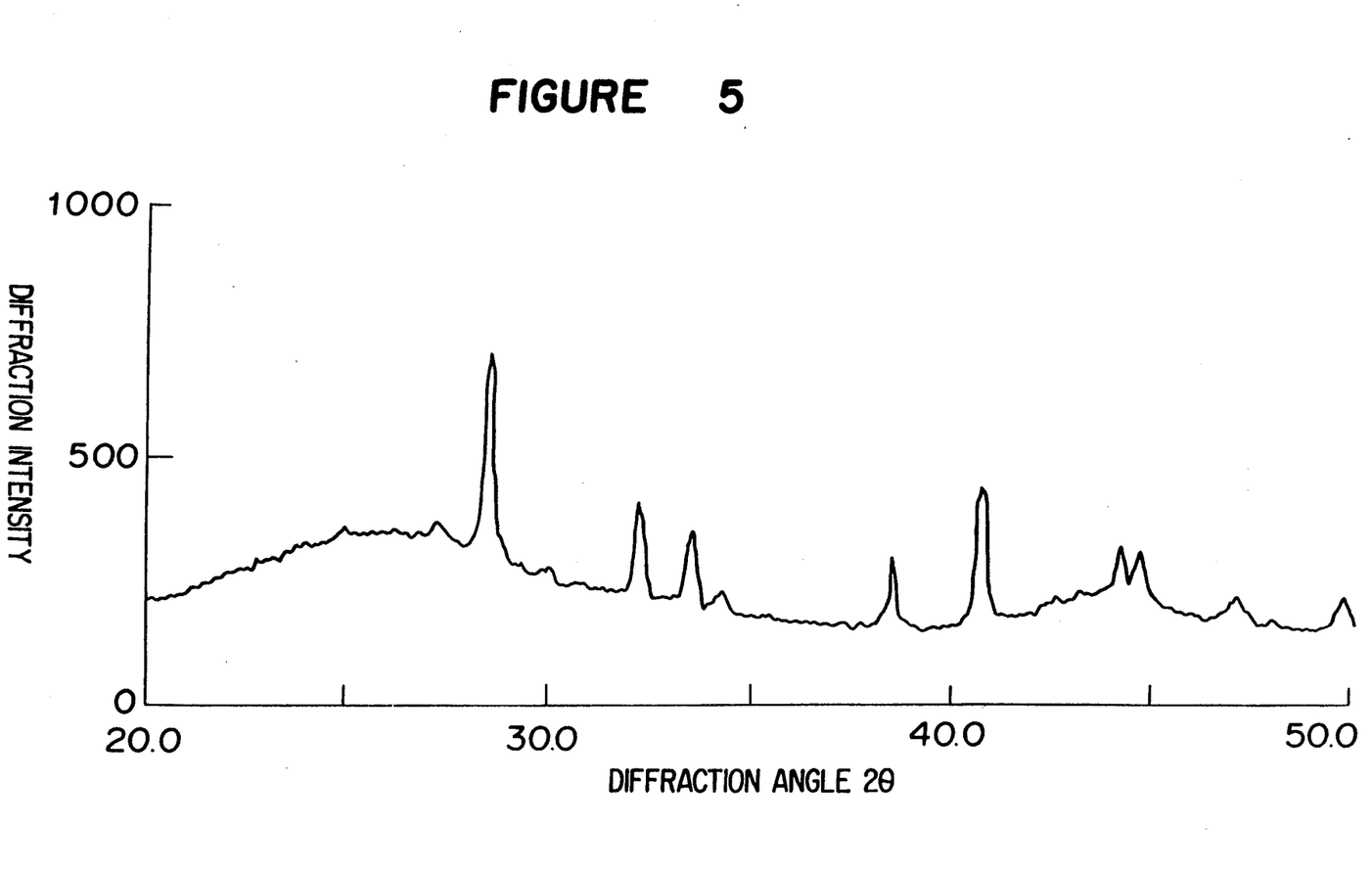
FIG. 5 is a similar X-ray diffraction pattern of a Te-Fe-KCl catalyst supported on active carbon.

A Te-Fe-KCl catalyst supported on active carbon was prepared in the same manner as in Example 1 except that 0.443 g of ferric chloride anhydride, 1.462 g of tellurium tetrachloride and 0.69 g of potassium chloride were used. The amount of supported Te in the catalyst thus prepared was 6%, and the atomic ratio of tellurium to iron was 2. Further, the amount of supported potassium chloride was 6%. The catalyst thus obtained was analyzed by X-ray diffraction whereby it was confirmed that a catalyst having the X-ray diffraction pattern of $FeTe_2$ and potassium chloride as shown in FIG. 5, was formed. Using 2 g of this catalyst, the reaction was conducted in the same manner as in Example 1. The results are shown in Table 13.

EXAMPLE 29

A Te-Pd-KCl catalyst supported on active carbon was prepared in the same manner as in Example 1 except that 1.083 g of palladium chloride, 1.647 g of tellurium tetrachloride and 1.56 g of potassium chloride were used. The amount of supported Te in the catalyst thus prepared was 6%, and the atomic ratio of tellurium to palladium was 1. Further, the amount of supported potassium chloride was 12%. The reaction was conducted in the same manner as in Example 1 except that 2 g of this catalyst was used. The results are shown in Table 13.

EXAMPLE 30

A Te-Pd alloy catalyst supported on active carbon was prepared in the same manner as in Example 1 except that 0.981 g of palladium chloride and 1.491 g of tellurium tetrachloride were used. In 20 ml of distilled water, 0.47 g of cesium chloride was dissolved, and to this solution, the Te-Pd alloy catalyst previously prepared was added. Upon expiration of 20 hours, the aqueous solution was dried on a warm bath of 80° C. Further, drying was conducted in a glass tube where the temperature was raised from room temperature to 150° C. at a rate of 10° C. per minute under a nitrogen stream and then maintained at 150° C. for one hour. The amount of supported Te in the catalyst thus prepared was 6% as metal, and the atomic ratio of tellurium to palladium was 1. Further, the amount of supported cesium chloride was 4%. The reaction was conducted in the same manner as in Example 1 except that 2 g of this catalyst was used. The results are shown in Table 13.

EXAMPLE 31

In 20 ml of distilled water, 0.72 g of sodium chloride was dissolved. Then, 10 g of active carbon treated in the same manner as in Example 1 was added thereto. Upon expiration of 20 hours, the aqueous solution was dried on a warm bath of 80° C. Further, drying was conducted in a glass tube where the temperature was raised from room temperature to 150° C. at a rate of 10° C. per minute under a nitrogen stream, and then maintained at 150° C. for one hour. Then, 1.270 g of palladium acetate and 1.527 g of tellurium tetrachloride were dissolved in 40 ml of acetone, and to this solution, active carbon having sodium chloride supported thereon, was added. Upon expiration of 20 hours, the acetone solution was dried on a warm bath of 60° C. Further, drying was conducted in a glass tube wherein temperature was raised from room temperature to 150° C. at a rate of 10° C. per minute in a nitrogen stream and then maintained at 150° C. for one hour. Then, in that state, the temperature was lowered to room temperature. The nitrogen stream was replaced by a gas comprising 10% of hydrogen and the rest being nitrogen, and the total flow rate was changed to 200 ml/min. The temperature was raised from room temperature to 150° C. at a rate of 10° C. per minute and then maintained at 150° C. for two hours. Further, the temperature was raised to 400° C. at a rate of 10° C. per minute and then maintained at 400° C. for one hour to obtain Te-Pd-NaCl catalyst supported on active carbon.

The amount of supported Te in the catalyst thus prepared was 6% as metal, and the atomic ratio of tellurium to palladium was 2. Further, the amount of supported sodium chloride was 6%. The reaction was conducted in the same manner as in Example 1 except that 2 g of this catalyst was used. The results are shown in Table 13.

TABLE 1

| Lattice plane distance (d value) | Relative intensity |
| --- | --- |
| 2.86 | 100 |
| 2.10 | 41 |
| 1.95 | 21 |
| 1.61 | 12 |
| 1.58 | 15 |
| 1.575 | 13 |

Measuring conditions: 40 kV, 24 mA and CuKα-line

TABLE 2

| | Temp. (°C.) | Propylene conversion (%) | AC | Selectivities (%) | | |
| --- | --- | --- | --- | --- | --- | --- |
| | | | | i-PrCl | CO + $CO_2$ | Others* |
| Example 1 | 150 | 79.5 | 7.7 | 91.6 | 0.1 | 0.6 |
| | 180 | 69.2 | 41.3 | 52.1 | 0.5 | 6.1 |
| | 210 | 60.1 | 61.0 | 26.7 | 1.4 | 10.9 |
| | 240 | 42.2 | 70.9 | 12.9 | 3.7 | 12.5 |
| Example 2 | 210 | 39.7 | 45.0 | 42.9 | 1.6 | 10.5 |
| | 300 | 42.2 | 68.1 | 2.9 | 10.5 | 18.5 |
| Example 3 | 210 | 63.0 | 59.5 | 10.6 | 2.9 | 27.0 |
| Example 4 | 210 | 40.2 | 49.0 | 41.2 | 2.4 | 7.4 |
| Example 5 | 210 | 45.7 | 25.1 | 61.7 | 2.0 | 11.2 |
| Example 6 | 210 | 36.3 | 35.1 | 52.7 | 3.0 | 9.2 |

AC: allyl chloride i-PrCl: isopropyl chloride
*Others: 1,2-dichloropropane, 1-chloropropene, etc.

TABLE 3

| Lattice plane distance (d value) | Relative intensity |
| --- | --- |
| 5.07 | 4 |
| 2.87 | 100 |
| 2.56 | 2 |
| 2.06 | 41 |
| 2.01 | 48 |
| 1.87 | 2 |
| 1.65 | 17 |
| 1.58 | 3 |
| 1.53 | 7 |
| 1.44 | 8 |

Measuring conditions: 40 kV, 24 mA and CuKα-line

TABLE 4

| | Temp. (°C.) | Propylene conversion (%) | AC | Selectivities (%) | | |
| --- | --- | --- | --- | --- | --- | --- |
| | | | | i-PrCl | CO + $CO_2$ | Others* |
| Example 7 | 150 | 45.6 | 12.0 | 87.3 | 0.1 | 0.6 |
| | 180 | 43.7 | 37.4 | 58.5 | 0.3 | 3.8 |
| | 210 | 46.3 | 64.6 | 25.8 | 1.4 | 8.2 |
| | 240 | 51.2 | 78.1 | 5.6 | 3.9 | 12.4 |
| Example 8 | 210 | 42.5 | 48.0 | 38.0 | 1.5 | 12.5 |
| | 300 | 32.3 | 54.1 | 3.2 | 15.2 | 27.5 |
| Example 9 | 210 | 31.8 | 32.8 | 47.4 | 3.6 | 16.2 |
| Example 10 | 210 | 8.2 | 29.9 | 44.1 | 4.5 | 21.5 |
| Example 11 | 210 | 32.2 | 48.4 | 39.0 | 2.2 | 10.4 |
| Example 12 | 240 | 2.5 | 67.9 | 19.0 | 4.6 | 8.5 |
| Example 13 | 210 | 7.8 | 33.1 | 56.4 | 5.8 | 4.7 |
| Example 14 | 240 | 13.8 | 37.2 | 51.5 | 2.7 | 8.6 |
| Example 15 | 270 | 5.7 | 13.9 | 79.8 | 2.3 | 4.0 |
| Example 16 | 300 | 13.7 | 62.0 | 14.0 | 3.4 | 20.6 |
| Example 17 | 240 | 36.0 | 59.2 | 17.9 | 6.8 | 16.1 |

AC: allyl chloride i-PrCl: isopropyl chloride
*Others: 1,2-dichloropropane, 1-chloropropene, etc.

TABLE 5

| Lattice plane distance (d value) | Relative intensity |
| --- | --- |
| 3.20 | 25 |
| 2.86 | 100 |
| 2.61 | 72 |
| 2.26 | 21 |
| 1.93 | 73 |
| 1.77 | 27 |
| 1.71 | 38 |
| 1.40 | 19 |

Measuring conditions: 40 kV, 24 mA and CuKα-line

TABLE 6

| | Temp. (°C.) | Propylene conversion (%) | AC | Selectivities (%) | | |
| --- | --- | --- | --- | --- | --- | --- |
| | | | | i-PrCl | CO + $CO_2$ | Others* |
| Example 18 | 180 | 50.5 | 41.4 | 53.6 | 0.8 | 4.2 |
| | 210 | 60.9 | 74.1 | 18.8 | 0.9 | 6.2 |
| | 240 | 62.2 | 80.3 | 7.5 | 3.2 | 9.0 |
| | 270 | 52.6 | 76.5 | 3.2 | 6.2 | 14.1 |

AC: allyl chloride i-PrCl: isopropyl chloride
*Others: 1,2-dichloropropane, 1 chloropropene, etc.

TABLE 7

| Lattice plane distance (d value) | Relative intensity |
| --- | --- |
| 3.78 | 6 |
| 3.60 | 4 |
| 3.23 | 100 |
| 2.36 | 45 |
| 2.21 | 37 |
| 2.19 | 4 |
| 2.00 | 9 |
| 1.82 | 14 |
| 1.61 | 10 |
| 1.48 | 10 |
| 1.41 | 10 |

TABLE 7-continued

| Lattice plane distance (d value) | Relative intensity |
|---|---|
| 1.40 | 4 |

Measuring conditions: 40 kV, 24 mA and CuKα-line

TABLE 8

| | Temp. (°C.) | Propylene conversion (%) | Selectivities (%) | | | |
|---|---|---|---|---|---|---|
| | | | AC | i-PrCl | CO + $CO_2$ | Others* |
| Example 19 | 150 | 76.3 | 9.5 | 88.9 | 1.2 | 0.4 |
| | 180 | 62.2 | 44.2 | 52.7 | 0.5 | 2.6 |
| | 210 | 53.0 | 72.8 | 19.4 | 1.8 | 6.0 |

AC: allyl chloride i-PrCl: isopropyl chloride
*Others: 1,2-dichloropropane, 1-chloropropene, etc.

TABLE 9

| Lattice plane distance (d value) | Relative intensity |
|---|---|
| 3.17 | 100 |
| 2.35 | 29 |
| 2.22 | 4 |
| 2.14 | 22 |
| 2.03 | 7 |
| 1.98 | 4 |
| 1.77 | 8 |
| 1.69 | 4 |
| 1.58 | 6 |

Measuring conditions: 40 kV, 24 mA and CuKα-line

TABLE 10

| | Temp. (°C.) | Propylene conversion (%) | Selectivities (%) | | | |
|---|---|---|---|---|---|---|
| | | | AC | i-PrCl | CO + $CO_2$ | Others* |
| Example 20 | 210 | 61.1 | 79.6 | 13.1 | 1.2 | 6.1 |
| Example 21 | 210 | 8.4 | 85.4 | 3.8 | 6.3 | 4.5 |

AC: allyl chloride i-PrCl: isopropyl chloride
*Others: 1,2-dichloropropane, 1-chloropropene, etc.

TABLE 11

| Lattice plane distance (d value) | Relative intensity |
|---|---|
| 3.29 | 25 |
| 3.13 | 19 |
| 2.81 | 100 |
| 2.71 | 74 |
| 2.65 | 14 |
| 2.45 | 2 |
| 2.07 | 37 |
| 2.02 | 1 |
| 1.94 | 12 |
| 1.85 | 21 |
| 1.79 | 1 |
| 1.74 | 4 |

Measuring conditions: 40 kV, 24 mA and CuKα-line

TABLE 12

| | Temp. (°C.) | Propylene conversion (%) | Selectivities (%) | | | |
|---|---|---|---|---|---|---|
| | | | AC | i-PrCl | CO + $CO_2$ | Others* |
| Example 22 | 210 | 62.1 | 80.7 | 14.8 | 1.0 | 3.5 |
| Example 23 | 220 | 4.9 | 56.7 | 38.6 | 2.7 | 2.0 |
| Example 24 | 210 | 58.9 | 77.0 | 16.5 | 1.2 | 5.3 |
| Example 25 | 180 | 41.2 | 46.5 | 50.9 | 0.3 | 2.3 |
| | 210 | 52.3 | 78.3 | 15.8 | 1.4 | 4.5 |
| | 240 | 52.1 | 82.3 | 5.6 | 3.4 | 8.7 |

TABLE 12-continued

| | Temp. (°C.) | Propylene conversion (%) | Selectivities (%) | | | |
|---|---|---|---|---|---|---|
| | | | AC | i-PrCl | CO + $CO_2$ | Others* |
| Example 26 | 200 | 32.9 | 68.8 | 29.4 | 0.1 | 1.7 |
| Example 27 | 210 | 14.9 | 90.3 | 8.4 | 0.7 | 0.6 |

AC: allyl chloride i-PrCl: isopropyl chloride
*Others: 1,2-dichloropropane, 1-chloropropene, etc.

TABLE 13

| | Temp. (°C.) | Propylene conversion (%) | Selectivities (%) | | | |
|---|---|---|---|---|---|---|
| | | | AC | i-PrCl | CO + $CO_2$ | Others* |
| Example 28 | 210 | 59.1 | 82.2 | 10.4 | 1.8 | 5.6 |
| Example 29 | 180 | 35.6 | 30.6 | 66.0 | 0.2 | 3.2 |
| | 210 | 39.0 | 57.8 | 32.3 | 1.7 | 8.2 |
| | 240 | 42.1 | 70.2 | 11.7 | 3.7 | 14.4 |
| Example 30 | 210 | 39.4 | 49.2 | 40.7 | 2.1 | 8.0 |
| Example 31 | 240 | 38.4 | 64.2 | 16.9 | 4.5 | 14.4 |

AC: allyl chloride i-PrCl: isopropyl chloride
*Others: 1,2-dichloropropane, 1-chloropropene, etc.

We claim:

1. A method for producing allyl chloride by oxychlorination of propylene, which comprises reacting propylene, hydrogen chloride and oxygen in the presence of a catalyst comprising ana alloy of tellurium with a member selected from the group consisting of metals of groups VIII, Va and Ib of the Periodic Table, supported on a carrier.

2. The method according to claim 1, wherein the alloy of tellurium is supported on the carrier in an amount of from 0.1 to 50% by weight in terms of tellurium to the total amount by weight of the catalyst.

3. The method according to claim 1, wherein the alloy is an alloy of tellurium with a metal selected from the group consisting of iron, cobalt, nickel, palladium, ruthenium, iridium, antimony, bismuth and copper at an atomic ratio of tellurium to said metal within a range of from 40:1 to 1:20.

4. The method according to claim 1, wherein the catalyst contains an alkali metal salt supported on the carrier.

5. The method according to claim 4, wherein the alkali metal salt is an alkali metal chloride, nitrate, sulfate, acetate, oxide, naphthenate or oxalate.

6. The method according to claim 4, wherein the alkali metal salt is lithium chloride, sodium chloride, potassium chloride, cesium chloride, potassium nitrate, cesium nitrate, potassium sulfate, cesium sulfate, potassium acetate or cesium acetate.

7. The method according to claim 4, wherein the alkali metal salt is supported on the carrier in an amount of from 0.01 to 30% by weight to the total amount by weight of the carrier, the alloy of tellurium and the alkali metal salt.

8. The method according to claim 1, wherein the reaction is conducted in a gas phase at a temperature of from 100° to 400° C. under a pressure of from atmospheric pressure to 50 atm.

9. The method according to claim 1, wherein the carrier is silica, alumina, magnesia, zirconia, titania or active carbon.

10. The method according to claim 1, wherein said alloy of tellurium has an atomic ratio of tellurium to said member within a range of from 40:1 to 1:20.

* * * * *